United States Patent [19]

Franssen et al.

[11] Patent Number: 5,753,611
[45] Date of Patent: May 19, 1998

[54] PHARMACEUTICAL COMPOSITION HAVING SITE-SPECIFIC DELIVERY

[75] Inventors: Erik J. F. Franssen, Groningen; Frits Moolenaar, Stitswerd; Dirk K. F. Meijer; Dick De Zeeuw, both of Groningen, all of Netherlands

[73] Assignee: Rijksuniversiteit Groningen, Groningen, Netherlands

[21] Appl. No.: 302,749

[22] PCT Filed: Mar. 15, 1993

[86] PCT No.: PCT/NL93/00061

§ 371 Date: Nov. 4, 1994

§ 102(e) Date: Nov. 4, 1994

[87] PCT Pub. No.: WO93/17713

PCT Pub. Date: Sep. 16, 1993

[30] Foreign Application Priority Data

Mar. 13, 1992 [NL] Netherlands ............................. 9200481

[51] Int. Cl.$^6$ .................. A61K 38/00; A61K 31/22; A61K 31/185
[52] U.S. Cl. .................. 514/2; 514/546; 514/547; 514/553; 424/422; 435/174; 435/177; 435/181; 530/810; 530/812; 530/815
[58] Field of Search .................. 424/422, 489, 424/499, 500, 501; 530/810, 812, 815, 816, 380, 391.1, 395.5; 514/546, 547, 2, 553; 560/179, 180; 435/183, 174, 177, 181

[56] References Cited

PUBLICATIONS

Larsen, "Macromolecular prodrugs, XII. Kinetics of release of naproxen from various polysaccharide ester prodrugs in neutral and alkaline solution", *International Journal of Pharmaceutics*, vol. 51, No. 3, May 1, 1989, pp. 233–240.

Franssen et al., "Low Molecular Weight Proteins as Carriers for Renal Drug Targeting. Preparation of Drug–Protein Conjugates and Drug–spacer Derivatives and Their Catabolism in Renal Cortex Homogenates and Lysosomal Lysates", *Journal of Medicinal Chemistry*, vol. 35, Apr. 1992, pp. 1246–1259.

Duncan, Selective Endocytosis of Macromolecular Drug Carriers. p. 587, Marcel Dekker, 1987.

Meijer Antiviral Res. 18, 1992 215–258.

*Primary Examiner*—Gollamudi S. Kishore
*Attorney, Agent, or Firm*—Oliff & Berridge, PLC

[57] ABSTRACT

Use of α-hydroxy acids and poly-α-hydroxy acids as spacer between a therapeutically and/or diagnostically active compound and a soluble macromolecular carrier in pharmaceutical compositions having site-specific delivery. In one embodiment glycolic acid, L-lactic acid or tetra-L-lactic acid is used as spacer between a non-steroidal anti-inflammatory substance and a carrier of low molecular protein (LMWP).

19 Claims, No Drawings

PHARMACEUTICAL COMPOSITION HAVING SITE-SPECIFIC DELIVERY

This application is a 371 of PCT/NL/93/00061, filed Mar. 15, 1993.

The invention relates to a pharmaceutical composition having site-specific and in particular tissue-specific delivery, in addition to a method for producing same.

Pharmaceutical compositions having site-specific delivery are sometimes made by starting from an inactive variant ("prodrug") of a therapeutically or diagnostically active substance which is converted into the active form only after reaching a determined place in the body such as a specific organ or tissue. Another possibility is the combining of the active substance with a pharmaceutical carrier in particle form, such as liposomes for instance, or a soluble macromolecular carrier, such as polypeptides for instance, which have a preference for a specific place in the human or animal body and there release the active substance.

In the case that a polypeptide or other soluble macromolecular material is used as carrier for the active substance, it is preferred to couple this carrier with the active substance by covalent bonds. On arrival at the desired location in the body these covalent bonds then have to be broken, this such that the active substance is released. Problems can however occur here. Despite the fact that many macromolecular carriers are biologically degradable, they sometimes do not release the active substance in the correct form or at the desired rate. In order to obviate this problem molecules of a compound serving as spacer can be linked between the active substance and the carrier, but the selection of a suitable spacer results in turn in new problems. With a view to an efficient and/or controlled decoupling of the active substance and the carrier, particular attention must be given to the nature of the active substance, the type of covalent bond of the active substance to the spacer and also to the length and branching degree of the spacer. The spacer itself and its breakdown products must further be non-toxic.

It has now been found during further research that α-hydroxy acids and poly-α-hydroxy acids are eminently suitable for use as spacer between an active substance and a soluble macromolecular carrier provided the active substance has a terminal carboxyl group. The α-hydroxy acids can namely be bonded by esterification (between the α-hydroxy group of the α-hydroxy acid and the carboxyl group of the active substance) to the active substance and be moreover coupled by any covalent bond (between the carboxyl group of the α-hydroxy acid and a reactive group of the macromolecular carrier) to the soluble macromolecular carrier. Both types of bonds are normally resistant to the conditions in the bloodstream of a human or animal body but, after arrival at a tissue at which the macromolecular carrier is specifically targeted, the ester bond between active substance and spacer could easily be broken by enzymes (esterases), so that the active substance is released in the original (active) form. Since the α-hydroxy acids and poly-α-hydroxy acids are not toxic and allow of relatively easy coupling and decoupling, they represent an attractive option for the selection of a spacer in pharmaceutical compositions of the stated type. It has moreover been found that the rate of delivery of the active substance into the desired tissues can be controlled by variation of the type of α-hydroxy acid and also by variation of the length and/or the branching degree of the poly-α-hydroxy acid that is used as spacer in the pharmaceutical composition.

The invention therefore provides a pharmaceutical composition having site-specific delivery and comprising:

at least one therapeutically and/or diagnostically active compound, said compound having a terminal carboxyl group, a soluble macromolecular pharmaceutical carrier, and an α-hydroxy acid or poly-α-hydroxy acid functioning as a spacer between active compound and carrier and being coupled through an ester bond to the active compound and through any covalent bond to the carrier with the exception of the conjugate of dextran and naproxen linked via a glycolic acid spacer. This conjugate was already disclosed in an article of Larsen, C. in International Journal of Pharmaceutics 51, 233–240 (1989).

The spacer for use in the composition according to the invention is an α-hydroxy acid or poly-α-hydroxy acid. Suitable examples are monobasic α-hydroxy acids such as glycolic acid and lactic acid as well as dibasic and tribasic α-hydroxy acids such as malic acid, citramalic acid, tartaric acid and citric acid. Understood by poly-α-hydroxy acids are compounds which are formed by linking together (mutual esterification) of two or more molecules of α-hydroxy acid; a suitable example is tetra-L-lactic acid which consists of four lactic acid units linked together.

Any therapeutically and/or diagnostically active compound which has a terminal carboxyl group can be coupled by means of the α-hydroxy acids or poly-α-hydroxy acids to a macromolecular pharmaceutical carrier. Suitable for use are for instance the substances known as "non-steroidal anti-inflammatory drugs" (NSAID), with as suitable examples acetylsalicylic acid, (S) -6-methoxy-α-methyl-2-naphthalene acetic acid and the like.

Any soluble macromolecular pharmaceutical carrier can be coupled through the α-hydroxy acids and poly-α-hydroxy acids to a therapeutically and/or diagnostically active compound. These are generally proteins, glycoproteins, polypeptides and polyclonal or monoclonal antibodies which can each display a selective targeting to a specific tissue type or a specific type of tissue call. Monoclonal antibodies are for example targeted especially at tissues with a specific type of antigen, while glycoproteins with terminal sugar residues are particularly targeted at specific types of liver cell. Good results are achieved with a group of peptides known as Low Molecular Weight Proteins (LMWP) with as suitable examples lysozyme, cytochrome C and aprotein. These LMWPs are targeted specially at the kidneys. They are rapidly cleared out of the bloodstream by glomerular filtration and then quantitatively reabsorbed in the proximal tubular cells, whereafter they are broken down to amino acids by the lysosomes.

Good results were obtained with a pharmaceutical composition wherein the therapeutically active substance (S)-6-methoxy-α-methyl-2-naphthalene acetic acid was bonded via an α-hydroxy acid to lysozyme. It was found here that the composition remained stable in the bloodstream of experimental animals but was cleaved in the kidneys, wherein the therapeutically active substance was released in active form. It was also found here that the ester bonds in combinations with L-lactic acid are cleaved more rapidly than in combinations with glycolic acid and that chain lengthening of the spacer makes the ester bonds still better accessible for cleaving by enzymes. This indicates that all α-hydroxy acids and poly-α-hydroxy acids are usable as spacer and also creates the possibility of achieving a controlled delivery of the active substance into the tissues by variation of the type of α-hydroxy acid and by variation of the length and/or branching degree of the α-hydroxy acid or poly-α-hydroxy acid.

The compositions according to the invention can in general be produced by coupling an α-hydroxy acid or poly-α-hydroxy acid through esterification of the α-hydroxy group to a therapeutically or diagnostically active compound having a terminal carboxyl group on one side and coupling with its free carboxyl group through a covalent bond to a soluble macromolecular carrier on the other side. Both reactions can be performed in any manner usual for this purpose. The esterification can for instance be performed by allowing an acid chloride or other reactive derivative of the active compound to react directly with the α-hydroxy acid or poly-α-hydroxy acid. Another possibility is to apply one of the usual methods of peptide chemistry such as an esterification under the influence of dicyclohexylcarbodiimide. It is desirable in that case to initially protect the carboxyl group of the α-hydroxy acid or poly-α-hydroxy acid by arranging a protective group and after esterification to remove this protective group in the usual manner, for example with trifluoroacetic acid and anisole.

When the macromolecular carrier consists of a polypeptide the carboxyl group of the α-hydroxy acid or poly-α-hydroxy acid can be coupled to the amino group of a terminal amino acid in this polypeptide. Such a coupling can take place in a manner usual in peptide chemistry, for instance with a carbodiimide method or an N-hydroxysuccinimide or N-hydroxysulphosuccinimide method. Should the carrier consist of a protein, glycoprotein or of antibodies, similar procedures can then be followed.

The obtained coupling products can be purified in usual manner. For the purpose of the pharmaceutical application they can be complemented with usual excipients, diluents and additives. The composition obtained will generally take the form of an injection composition, but other dosage forms are not excluded. The dosage to be used will conform to the active substance incorporated in the composition.

There now follow a number of preparation examples and biological tests. The term "naproxen" refers to (S)-6-methoxy-α-methyl-2-naphthalene acetic acid.

EXAMPLE I

Naproxen-L-lactic acid-lysozyme

1) L-lactic acid-PMB. A suspension of L-lactic acid (1.5 g, 10 mmol) in dimethylformamide was treated with triethylamine (20 mmol) and pentamethylbenzyl chloride (PMBC1) (10 mmol). The mixture was heated carefully to obtain a solution and held at room temperature at night. Thereafter an excess of 1N NaHCO, was added. Within several minutes the ester separated out in crystalline form. The product was collected, washed with water and dried under vacuum.

Yield 95%. Melting point 115°–116° C. $^1$H NMR (CDCl$_3$): δ 5.27 (m, 2, CH$_2$), 4.23 (q, 1, CHCH$_3$), 2.27 (s, 15, CH$_3$—Cq), 1.47 (d, 3, CH$_3$CH).

2) Naproxen-L-lactic acid-PMB. Added to a solution of naproxen (2.3 g, 10 mmol), L-lactic acid-PMB (2.5 g, 10 mmol) and 4-dimethylamino-pyridine (1.22 g, 10 mmol) in 150 ml dichloromethane was a solution of dicyclohexylcarbodiimide (2.27 g, 11 mmol) in 50 ml dichloromethane. The reaction mixture was stirred at 25° C., wherein the progress of the reaction was followed with thin-layer chromatography. Thereafter the N,N-dicyclohexylurea was filtered off. The filtrate was washed with 1M KHSO$_4$ (2×20 ml), water (2×20 ml), and 5% NaHCO$_3$ (2×20 ml). The organic layer was dried above water-free sodium sulphate and evaporated dry in vacuo. The residue was washed with petroleum ether and held under high vacuum for many hours to obtain an analytically pure product.

Yield 70%. $^1$H NMR (CDCl$_3$): δ 7.69–7.12 (m, 6, aromatic), 5.27 (m, 2, CH$_2$), 5.10 (q, 1, CHCH$_3$ (lact)), 3.94 (q, 1, CHCH$_3$ (naproxen)), 3.93 (s, 3, CH$_3$O), 2.27 (s, 15, CH$_3$—Cq), 1.61 (d, 3, CH$_3$CH (naproxen)), 1.47 (d, 3, CH$_3$CH (lact)).

3) Naproxen-L-lactic acid. A mixture of naproxen-L-lactic acid-PMB (2.3 g, 5 mmol), anisole (12 ml) and trifluoroacetic acid (10 ml) was held at room temperature for 2 minutes. The excess of reagent was then removed under vacuum below 30° C. The residue was dissolved in dichloromethane (100 ml) and washed with water (4×20 ml). The organic layer was extracted with diethylether (2×50 ml). Acidifying with 6N HCl provided the product which was extracted with dichloromethane (4×25 ml). The washed and dried product (Na$_2$SO$_4$) was evaporated dry and the residue dried in vacuo at 50° C. The product was crystallized from dichloromethane/cyclohexane.

Yield 75%. $^1$H NMR (CDCl$_3$): δ 1055–1050 (br s, 1, OH), 7.54–6.93 (m, 6, aromatic), 4.97 (q, 1, CHCH$_3$ (lact)), 3.76 (q, 1, CHCH$_3$ (naproxen)), 3.69 (s, 1, CH$_3$O), $_1$.40 (d, 5, CH$_3$OH (naproxen)), 1.31 (d, 3, CH$_3$CH (lact)).

4) Naproxen-L-lactic acid-NHS. Naproxen-L-lactic acid (302 mg, 1 mmol) was dissolved in 10 ml dimethylformamide. Dicyclohexylcarbodiiaide (277 mg, 1.1 mmol) was then added. The solution was stirred for 15 minutes, whereafter N-hydroxysuccinimide (115 mg, 1 mmol) dried beforehand in vacuo for 24 hours at 50° C. was added. The mixture was stirred for 24 hours. After filtering off the precipitation the filtrate was evaporated dry in vacuo and the residue was washed with dry heptane. The residue was dissolved in ethylacetate, filtered, evaporated dry in vacuo and crystallized from dichloromethane/hexane.

Yield 91%. 1H NMR (CDCl$_3$): δ 7.5–6.9 (m, 6, aromatic), 5.0 (q, 1, CHCH$_3$ (lact)), 3.8 (q,1, CHCH$_3$), 3.7 (s, 3, CH$_3$O), 2.8 (s, 4, CH$_2$CH$_2$(NHS)), $_1$.5 (d, 3, CH$_3$ CH (naproxen)), 1.3 (d, 3, CH$_3$CH (lact)).

5) Naproxen-L-lactic acid-lysozyme. Naproxen-L-lactic acid-NHS (14.1 mg, 34.7 μmol) was dissolved in 10 ml DMF and placed in reaction for 2 hours with lysozyme (100 mg, 6.95 μmol) in a DMF/borate (0.025M; pH 8.5) (20/80) mixture. After filtration of the precipitated material the filtrate was purified by gel filtration. After a subsequent ultrafiltration (Amicon) and lyophylisation, the product was kept at −20° C. Yield 74%. The molar substitution degree was 0.6 as determined with a fluorimetric measurement of naproxen (excitation wavelength 330 nm, emission wavelength 360 nm) and a protein test according to Bradford (compare Bradford, Anal. Biochem. 72, 248 (1976)).

EXAMPLE II

Naproxen-ester derivatives.

In small-scale tests the acid chloride of naproxen (10.8 mg, 0.04 mmol) was dissolved together with glycolic acid (4 Mg, 0.04 mmol), L-lactic acid (5 mg, 0.04 mmol) or tetra-L-lactic acid (12.6 mg, 0.04 =mol) in dry dichloromethane. Triethylamine (11 microliters, 0.08 mmol) was added, whereafter the mixture was stirred for 18 hours. The progress of the reaction was followed with thin-layer chromatography. The obtained ester derivatives were purified by HPLC with reverse phase.

Several biological tests were carried out with the thus obtained products.

Test 1

During in vitro tests the naproxen esters obtained in Example II were incubated at diverse pH values with lysosomelyzates obtained from homogenates of rat kidneys.

At pH 5 it was found that 81% of the naproxen was released from the ester with glycolic acid within 24 hours. In contrast, 100% naproxen had already been released from an eater with L-lactic acid within 30 minutes. In the case of the ester of naproxen and tetra-L-lactic acid the ester bond was found to be still more sensitive to enzymatic cleaving in vitro.

Test 2

During in vivo tests male Wistar rats (280–310 g) were placed in metabolic cages where they had free access to food and water. After addition of 500 IU of heparin, 10 mg or 1 mg naproxen-L-lactic acid-lysozyme, freshly dissolved in blood plasma, was administered to the rats by intravenous injection. Plasma samples and urine samples were collected at regular intervals and analyzed. It was found that the injected products were sufficiently stable in blood plasma to reach the kidneys intact. It was further found that the whole dose was reabsorbed into the kidneys and locally metabolized to naproxen.

We claim:

1. A conjugate adapted for site-specific delivery of an active compound, said compound having an activity selected from the group consisting of therapeutic activity and diagnostic activity and having a terminal carboxyl group, wherein the active compound is linked via an ester bond to a spacer that is covalently bonded to a soluble proteinaceous macromolecular pharmaceutical carrier, the spacer being a monomer or polymer of an α-hydroxy acid, said α-hydroxy acid being selected from the group consisting of glycolic acid, L-lactic acid, malic acid, citramalic acid, tartaric acid and citric acid and wherein said conjugate is absorbable by a cell.

2. A conjugate as claimed in claim 1, wherein the spacer is tetra-L-lactic acid.

3. A conjugate as claimed in claim 1, wherein the active compound is a non-steroidal anti-inflammatory drug.

4. A conjugate as claimed in claim 3, wherein the active compound is (S)-naproxen.

5. A conjugate as claimed in claim 1, wherein the carrier is selected from the group consisting of glycoproteins, polypeptides and polyclonal or monoclonal antibodies.

6. A conjugate as claimed in claim 5, wherein the carrier is a low molecular weight protein.

7. A conjugate as claimed in claim 6, wherein the carrier is a lysozyme.

8. A method of producing a conjugate as claimed in claim 1, which comprises providing the spacer, said spacer having an α-hydroxy group and a free carboxyl group; coupling the spacer through esterification of the α-hydroxy group to the active compound; and covalently bonding the spacer with the free carboxyl group to the macromolecular carrier.

9. A conjugate according to claim 1, wherein said α-hydroxy acid is selected from the group consisting of glycolic acid and L-lactic acid.

10. A conjugate according to claim 9, wherein the active compound is a non-steroidal anti-inflammatory drug.

11. A conjugate according to claim 9, wherein the carrier is selected from the group consisting of glycoproteins, polypeptides and polyclonal or monoclonal antibodies.

12. A conjugate according to claim 9, wherein the carrier is a low molecular weight protein.

13. A conjugate according to claim 12, wherein the carrier is a lysozyme.

14. A method of producing the conjugate according to claim 10, said method comprising providing the spacer, said spacer having an α-hydroxy group and a free carboxyl group; coupling the spacer through esterification of the α-hydroxy group to the active compound; and covalently bonding the spacer with the free carboxyl group to the carrier.

15. A pharmaceutical composition comprising the conjugate according to claim 1 and an excipient.

16. A composition according to claim 15, wherein said composition is suitable for injection.

17. A composition according to claim 16, wherein said injection is intravenous.

18. A method of diagnosing or treating a condition responsive to said active compound in a patient comprising administering to said patient a composition according to claim 15.

19. A method according to claim 18, wherein said administering is by intravenous injection.

* * * * *